United States Patent
Stein et al.

(10) Patent No.: US 7,247,311 B2
(45) Date of Patent: Jul. 24, 2007

(54) APPARATUS AND METHODS FOR CONTROLLING INSECTS IN BUILDINGS AND AGRICULTURAL USES

(75) Inventors: Jerman O. Stein, Shelby, NC (US); Earl Tryon, Marietta, GA (US)

(73) Assignee: Agrinova Corporation, Bowle, MD (US)

( * ) Notice: Subject to any disclaimer, the term of this patent is extended or adjusted under 35 U.S.C. 154(b) by 610 days.

(21) Appl. No.: 10/158,605

(22) Filed: May 30, 2002

(65) Prior Publication Data

US 2002/0197295 A1    Dec. 26, 2002

Related U.S. Application Data

(63) Continuation-in-part of application No. 09/397,272, filed on Sep. 16, 1999, now abandoned.

(51) Int. Cl.
    *A01N 25/34*    (2006.01)
    *A01N 53/06*    (2006.01)
(52) U.S. Cl. ............... 424/403; 424/405; 424/406; 424/409; 424/411; 514/531
(58) Field of Classification Search ............... 424/403, 424/405, 406, 409, 411; 514/531
    See application file for complete search history.

(56) References Cited

U.S. PATENT DOCUMENTS

| | | |
|---|---|---|
| 2,023,270 A | 12/1935 | Fischer |
| 2,899,771 A | 8/1959 | Burris |
| 3,454,510 A | 7/1969 | Newland et al. |
| 3,771,254 A | 11/1973 | Scott et al. |
| 3,857,934 A | 12/1974 | Bernstein et al. |
| 3,864,468 A | 2/1975 | Hyman et al. |
| 3,931,692 A | 1/1976 | Hermanson |
| 3,996,348 A | 12/1976 | Greenberg |
| 4,008,351 A | 2/1977 | Inoue et al. |
| 4,103,450 A | 8/1978 | Whitcomb |
| 4,123,518 A | 10/1978 | Behrenz et al. |
| 4,128,529 A | 12/1978 | Becker et al. |
| 4,198,782 A * | 4/1980 | Kydonieus et al. ............ 47/58 |

(Continued)

FOREIGN PATENT DOCUMENTS

GB    1052998    * 12/1966

(Continued)

OTHER PUBLICATIONS

FMC Corporation, "Don't Let Termites Eat You Out of House and Home.", Brochure, 1994, pp. 1-10, USA.

*Primary Examiner*—Neil S. Levy
(74) *Attorney, Agent, or Firm*—Bacon & Thomas, PLLC

(57) ABSTRACT

Insect barriers for building structures include rigid foam sheets and sheets of film or mesh formed of polymer material impregnated throughout with a synthetic pyrethroid insecticide such as permethrin. Foam sheets are applied to exterior and interior surfaces of foundation walls to provide both thermal and insect barrier functions. Film and/or mesh sheets are positioned around exterior and interior perimeters of foundation walls to form skirts serving as insect barriers. Plant containers for containing growing plants are formed of polymer material impregnated throughout with a synthetic pyrethroid insecticide. Agricultural mulching film for covering the soil beneath and around a growing plant is formed of polymer material impregnated throughout with synthetic pyrethroid insecticide.

6 Claims, 7 Drawing Sheets

U.S. PATENT DOCUMENTS

| | | | |
|---|---|---|---|
| 4,215,508 | A | 8/1980 | Allen et al. |
| 4,320,113 | A | 3/1982 | Kydonieus |
| 4,350,678 | A | 9/1982 | Palvarini et al. |
| 4,552,752 | A | 11/1985 | Amick |
| 4,666,706 | A | 5/1987 | Farquharson et al. |
| 4,769,242 | A * | 9/1988 | Shibanai ..................... 424/411 |
| 4,793,474 | A | 12/1988 | Drake |
| 4,820,519 | A | 4/1989 | Gillette |
| 4,830,855 | A | 5/1989 | Stewart |
| 4,888,174 | A * | 12/1989 | Farquharson et al. ....... 424/405 |
| 4,908,980 | A | 3/1990 | Sherman |
| 4,978,530 | A | 12/1990 | Strong |
| 5,094,028 | A | 3/1992 | Hume |
| 5,094,847 | A | 3/1992 | Yazaki et al. |
| 5,156,843 | A | 10/1992 | Leong et al. |
| 5,178,495 | A | 1/1993 | Cameron |
| 5,194,323 | A | 3/1993 | Savoy |
| 5,224,288 | A | 7/1993 | Skelton et al. |
| 5,233,787 | A | 8/1993 | Andersen |
| 5,359,806 | A | 11/1994 | Jeffery et al. |
| 5,360,609 | A | 11/1994 | Wellinghoff |
| 5,526,607 | A | 6/1996 | Roesch et al. |
| 5,641,499 | A | 6/1997 | Bencsits |
| 5,707,736 | A | 1/1998 | Levy et al. |
| 5,801,194 | A | 9/1998 | Voris et al. |
| 5,811,461 | A | 9/1998 | Hackler et al. |
| 5,849,317 | A | 12/1998 | Shorey et al. |
| 5,860,266 | A | 1/1999 | Martinet et al. |
| 5,886,221 | A | 3/1999 | Sbragia et al. |
| 6,156,322 | A | 12/2000 | Alcott et al. |
| 6,156,328 | A * | 12/2000 | Alcott et al. ................. 424/405 |
| 6,803,051 | B1 * | 10/2004 | Voris et al. ................. 424/406 |

FOREIGN PATENT DOCUMENTS

| | | | |
|---|---|---|---|
| JP | 56-26811 A | | 3/1981 |
| JP | 56-100882 A | | 8/1981 |
| JP | 61-137803 | * | 6/1986 |
| NL | 6902500 | | 8/1970 |
| WO | WO9518532 | | 7/1995 |
| WO | WO9747190 | | 12/1997 |

* cited by examiner

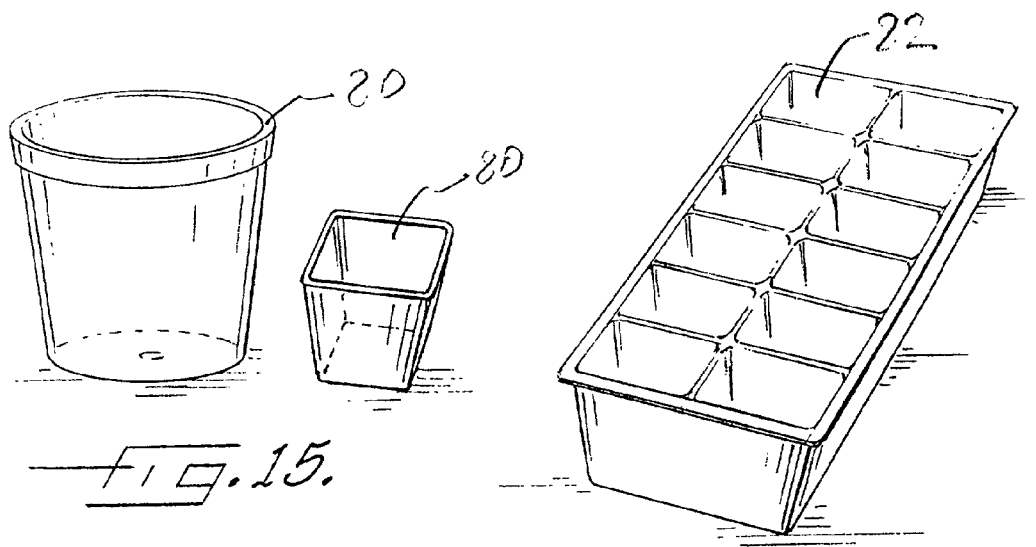
Fig. 15.
Fig. 16.
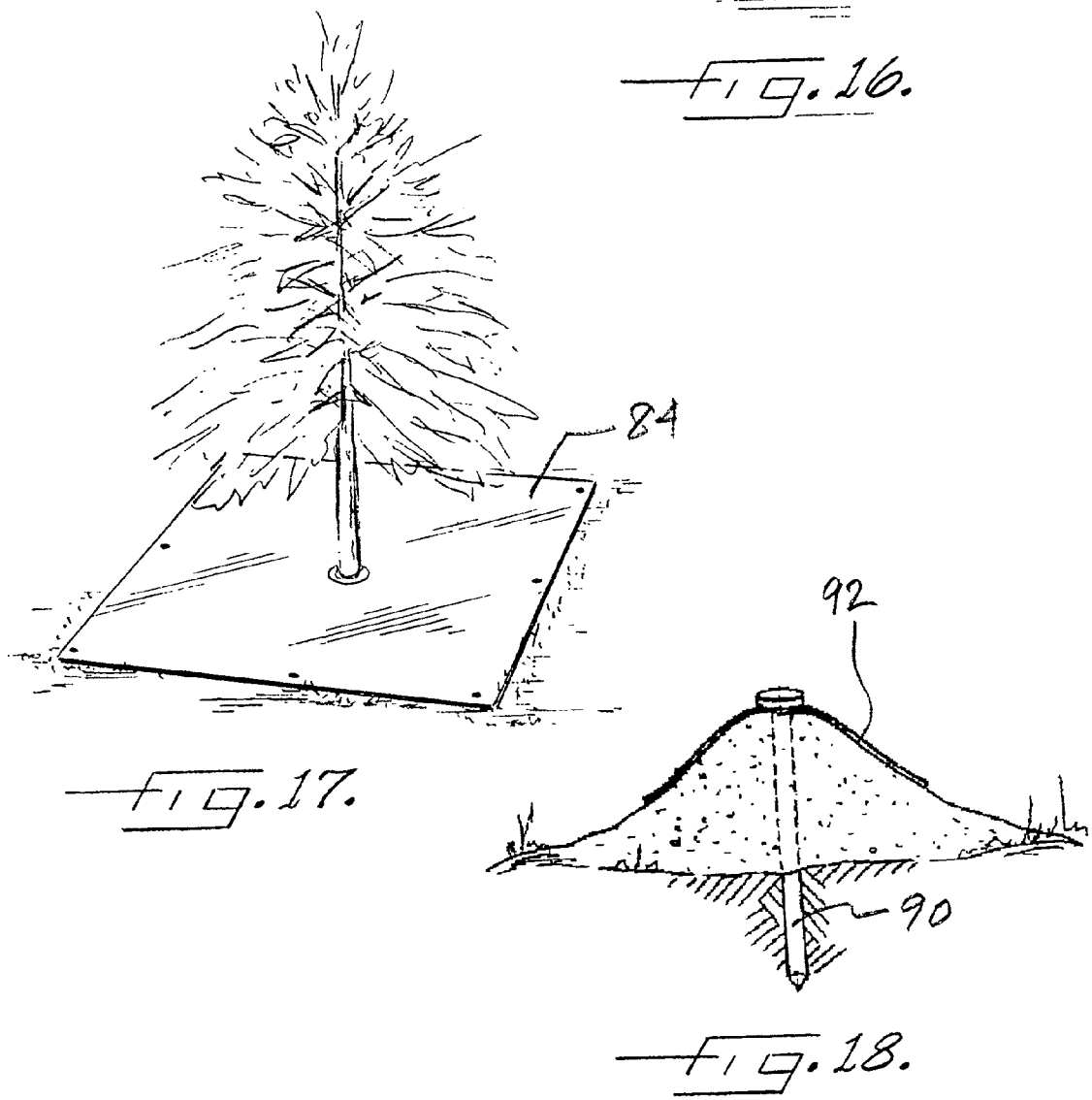
Fig. 17.
Fig. 18.

APPARATUS AND METHODS FOR CONTROLLING INSECTS IN BUILDINGS AND AGRICULTURAL USES

CROSS-REFERENCE TO RELATED APPLICATION

This application is a continuation-in-part of U.S. patent application Ser. No. 09/397,272 filed Sep. 16, 1999, now abandoned.

FIELD OF THE INVENTION

The invention relates generally to apparatus and methods for controlling insects, and more particularly relates to apparatus and methods for providing barriers against intrusion of insects into building structures and for preventing or discouraging insects from infesting growing plants, harvested produce, etc.

BACKGROUND OF THE INVENTION

Damage to building structures and plants caused by insects represents a formidable problem affecting a wide variety of construction and agricultural activities. Considerable effort is devoted by manufacturers of insecticides to develop safe and effective products for controlling such pests as ants, roaches, termites, and many others. An area of growing concern among manufacturers and regulators has been the impact that insecticides can have on the environment. In conventional methods for applying insecticides to control insects, the insecticide is typically applied in liquid, powder or granular form to the area in which it is desired to control insects. When the insecticide is applied onto soil or into an area of a building structure, there is a substantial likelihood that the insecticide, through the action of water or other mechanisms, will migrate from the area of application to other areas in which it is undesired. For instance, runoff of insecticides into waterways represents a serious environmental problem.

Additionally, insecticides applied in the conventional manner are subject to being degraded by dilution caused by water and by the action of microorganisms in the soil to which the insecticide is applied. The migration and degradation result in failure to provide long-term control. As a result, it typically is necessary to periodically re-apply insecticide to the area to be protected. Unfortunately, such re-application only exacerbates the environmental problems noted above.

For the above reasons, increasing attention is being paid to the development of controlled delivery devices for making insecticides available where they are needed while preventing the uncontrolled release or migration of the insecticide to undesired areas. U.S. Pat. No. 5,801,194 discloses a termite and boring insect ground barrier for protecting wooden structures, comprising a controlled release device formed as a sheet of spun-bonded polymer material having stripes or spots of a mixture of polymer and insecticide bonded thereto. The stripes are about one centimeter in height and spaced apart about 5 to 15 centimeters. The spots are about 0.5 to 1.5 centimeters in both diameter and height and are spaced apart about 1.5 to 4 centimeters. The '194 patent also discloses a foam sheet having pellets of the polymer and insecticide mixture embedded therein. The insecticide is present in the polymer in a concentration of about 5 to 30 percent by weight. The patent teaches placing the controlled release devices in various positions near a wooden structure to purportedly provide a means for a slow and relatively constant release of insecticide in order to create a barrier zone for insects in the soil around the structure. The controlled release devices are relatively complicated in their construction, which would likely render the devices prohibitively expensive to use in most building construction applications.

U.S. Pat. No. 2,899,771 discloses a two-layer insect resistant vapor barrier comprising a polyethylene film coated with a water soluble carrier impregnated with an insecticide. The '771 patent teaches placing the vapor barrier between a slab and the soil on which the slab is supported. Condensation forming on the vapor barrier is said to cause the insecticide to be released into the soil to act as a soil poison. With such a device, repellancy of insects is likely to be effective for only a relatively short period of time, as the carrier fully dissolves and releases all of the insecticide into the soil where it can be dispersed and/or broken down by the action of water and/or microorganisms in the soil.

U.S. Pat. No. 5,860,266 issued to Martinet et al. discloses a method for protection of buildings against termites, in which a non-porous film of plastic material impregnated throughout with a low concentration of an insecticide is laid over the entire erection surface of the soil prior to erection of the foundation and structure. Where intentional holes are made in the film, such as for the passage of pipes or conduits into the building, the soil near the holes is laced with pellets of plastic material impregnated with insecticide. The pellets are also applied to the soil in regions where unintentional or accidental tears or rips of the film may be likely, such as around the bottoms of foundation footers. The method relies on creating a plastic film barrier over the entire surface of the building foundation such that the barrier is between the foundation and the adjacent soil. A drawback of Martinet's method is that application of plastic film over the entire erection surface is not a standard building practice, and thus there may be some resistance to its adoption by construction contractors. Furthermore, the method is amenable only to new construction. Martinet does not teach any method for treating existing structures.

In some cases, certain standard or common construction practices can actually make it more difficult to protect a structure against termite infestation or to treat a structure that is already infested. For instance, a construction practice developed in Canada for energy-efficiency purposes comprises wrapping the foundation in thermally insulating foam board. This concept was adopted by the U.S. Department of Energy and was included in the federal Model Energy Code, which recommended installing foam insulation around slab foundations as much as four feet below ground. Accordingly, many builders in the late 1980s and early 1990s followed the Model Energy Code. Unfortunately, at about the same time, two insecticides that previously had been widely used for the control of termite infestation—chlordane and heptachlor—were banned by the U.S. Environmental Protection Agency. The insecticides that are now used instead have significantly less staying power in the soil and are less potent. It has since been found that many of the structures built with foam insulation near or below ground are subject to significant termite infestation problems, because the termites tunnel through and/or behind the insulation and are nearly impossible to eradicate. Spraying the foam insulation with insecticide does not work because the foam is waterproof.

In an effort to solve such problems, Clemson University researchers tried lacing foam board with boric acid, which kills termites if they ingest it. However, the researchers found that the boric acid did not prevent termites from building mud tunnels between the foam and the foundation. Thus, this apparent solution turned out to be a failure. In view of the problems associated with foam insulation, there are efforts in some states to prohibit the use of foam board in proximity to soil. It would be desirable, however, to be able to use foam insulation near soil because of the beneficial thermal insulative properties it possesses.

The agricultural industry is also significantly impacted by the damaged caused by insects. In the citrus industry, it is common practice to graft one variety of citrus plant into a hardy root stock of another variety. The root stock is selected, for example, to be drought-resistant, disease-resistant, etc., so that the citrus tree will survive and thrive from season to season and year to year. The fruit produced by the root stock, however, is undesirable, so a more-desirable variety is grafted into the root stock. The root stock typically extends about 12 inches or so above the soil line. Conventionally, citrus growers have wrapped the root stock with a thick plastic film or a polystyrene sleeve from the soil line up to about 18-24 inches above the soil line. This is done for one critical reason: The wrap prevents the root stock from putting out limbs that would produce unwanted fruit. However, in recent years, the practice of wrapping or sleeving root stock has been halted in some areas because certain insects, notably ants (including imported fire ants) and termites, take up nesting in the wraps or sleeves and tend to damage the plant stem, leaving the plant susceptible to disease if not killing the plant immediately. Attempts have been made to overcome this problem by placing a slow-release insecticide device between the plant stem and the wrap or sleeve. The slow-release device is a bag holding a quantity of insecticide and designed to slowly release insecticide from the bag. However, this solution is too costly to be practical. Thus, a more cost-effective solution to this problem is needed.

Furthermore, in the growing of many types of crops such as strawberries, tomatoes, eggplants, cucumbers, melons, squash, peppers, and others, it has been common practice to cover the soil with plastic film, also known as plastic mulch, for various purposes. The plastic mulch can be used to absorb solar energy and warm the soil in cooler climates so as to enable earlier crop production (or, alternatively, to reflect heat from the soil in warmer climates). The plastic mulch also improves moisture retention so that less irrigation is needed, inhibits growth of weeds, reduces leaching of fertilizer, and prevents contact of growing produce with soil and thus prevents rot and other soil contact-related damage. Another function of plastic mulch is to help insure that insecticidal fumigate injected into soil to control disease and insects remains in the soil, and to minimize release of toxic gases from the fumigate into the air. Methyl bromide is currently the fumigant used for this purpose, but EPA regulations promulgated to carry out the objectives of the U.S. Clean Air Act call for a gradual phaseout of methyl bromide over the next few years, with a complete ban becoming effective in 2005. Thus, an effective alternative to methyl bromide for growing crops is needed.

Yet another problem in the agriculture industry is unintentionally shipping insects with freshly harvested produce from grower to distributor to retailer. The case of the Mediterranean fruit fly is a classic example. Interstate and international shipments of produce can be subject to quarantine and rejection or destruction if the shipments are infested with particular pests. To avoid such a result, many shippers treat produce with low levels of pesticides to kill any insects on the produce prior to shipment. It would be desirable to have an alternative solution not involving the application of pesticides to the produce.

SUMMARY OF THE INVENTION

The above needs are met and other advantages are achieved by the present invention. One aspect of the invention provides devices and methods for forming barriers in building structures that not only provide insect repellancy, but also provide other desirable functions such as thermal insulation and/or moisture barrier protection. A significant advantage of the invention is that the materials used to provide the barrier devices are essentially the same as materials that are already commonly used in the construction trade, and the methods of applying the materials during the construction of a building are very similar to methods that are already commonly used. Thus, the devices and methods can be easily incorporated into a construction project without necessitating any radical changes in construction practices.

One aspect of the present invention relates to a barrier for providing both thermal insulation and insect repellancy for a building structure of the type erected upon a foundation that includes vertical foundation walls along a perimeter of the foundation. In a typical building of this type, the foundation walls have lower portions extending below a grade level of soil and upper portions extending above the grade level and having exterior and interior vertically extending surfaces. In accordance with a preferred embodiment of the invention, the barrier comprises a vertical thermal and insect barrier formed by exterior and interior rigid foam sheets applied respectively to the exterior and interior vertically extending surfaces of the foundation walls, the exterior and interior foam sheets extending above the grade level such that any insect pathway from soil along the foundation walls to the building is constrained to proceed along the foam sheets. The foam sheets comprise a rigid foam formed of a polymer material containing an insecticide of the pyrethroid family such that the insecticide is impregnated throughout the foam sheets. The foam sheets discourage insects from traveling from the soil along the foundation walls to the building.

Preferably, additional insect repellancy is provided by a flexible barrier disposed between the soil and the building inward of the foundation walls, the flexible barrier being formed of a polymer impregnated throughout with less than about two percent of a synthetic pyrethroid insecticide. The flexible barrier can comprise a continuous film of polymer impregnated with insecticide, or alternatively can comprise an open mesh defining openings therethrough. For example, the mesh can have openings measuring about ⅛-inch to ¼-inch across. Where the building is a slab construction having a horizontal slab, the flexible barrier is advantageously disposed along a lower surface of the slab between the slab and the soil.

The foam sheets advantageously comprise expanded polystyrene, which provides good thermal insulation properties. A preferred insecticide comprises permethrin, although other synthetic pyrethroids can be used, including deltamethrin, bifenthrin, and others as known to those of ordinary skill in the art. The insecticide is preferably present in the foam sheets in a concentration of less than about two percent by weight, and more preferably about one percent or less by weight. The invention thus runs counter to the teachings in the prior art, which suggests that foam board impregnated with boric acid does not protect a building structure against termites, and further suggests that substantially higher concentrations of insecticide (e.g., 5 to 30 percent as taught in U.S. Pat. No. 5,801,194) should be used in connection with foam insulation materials.

In accordance with a further preferred embodiment of the invention, the thermal and insect barrier further includes a horizontal thermal and insect barrier formed by horizontal foam sheets impregnated throughout with a synthetic pyrethroid insecticide and disposed between the soil and the building along an interior perimeter thereof defined by the foundation walls, the horizontal barrier having an outer edge adjacent the foundation walls and an inner edge spaced inwardly of the foundation walls. The horizontal barrier provides additional thermal insulation at the juncture between the vertical foundation walls and a horizontal slab or foundation floor of the building, and also discourages insects from migrating along a lower surface of the slab or floor to the outer perimeter of the slab where it meets with the walls of the structure. The flexible barrier advantageously overlaps at least a portion of the horizontal foam sheet barrier.

In a typical building, elongate members such as pipes and conduits extend from the soil through the foundation and into the building. Such pipes and conduits represent potential pathways for insects to travel along the exterior of the pipes from the soil into the building. Accordingly, the invention also includes barriers for preventing insects from traveling along pipes or conduits in this manner. Such a barrier comprises a horizontal foam sheet disposed between the soil and the building and defining an aperture through which the elongate member extends, the foam sheet being formed of a polymer impregnated throughout with a synthetic pyrethroid insecticide. The foam sheet advantageously has a thickness of at least about one inch. This barrier can be used alone or in combination with the previously described thermal and/or flexible barriers. The foam sheet surrounds the pipe and thus constrains an insect either to travel along the foam sheet or to attempt to travel between the inner surface of the aperture and the exterior of the pipe in order to reach the portion of the pipe that extends into the building. However, insects tend to avoid coming into close proximity to the treated foam sheet, and thus the foam sheet discourages insects from traveling along the pipe into the building.

Another aspect of the invention relates to insect barriers for building structures in which flexible sheets are used along exterior and interior perimeters of a foundation substantially at ground level and extending some distance above ground level. In accordance with a preferred embodiment of the invention, a barrier comprises an exterior perimeter barrier surrounding the outside perimeter of the building adjacent the exterior surfaces of the foundation walls, the exterior perimeter barrier comprising a flexible sheet formed of a polymer material impregnated throughout with a synthetic pyrethroid insecticide, the flexible sheet extending generally horizontally proximate an upper surface of the soil, the flexible sheet having an inward portion that extends upward above the soil along the exterior surfaces of the walls. The barrier further comprises an interior perimeter barrier surrounding the inside perimeter of the building adjacent the interior surfaces of the walls, the interior perimeter barrier comprising a flexible sheet formed of a polymer material impregnated throughout with a synthetic pyrethroid insecticide, the flexible sheet extending generally horizontally proximate an upper surface of the soil, the flexible sheet having an outward portion that extends upward above the soil along the interior surfaces of the walls. The exterior and interior perimeter barriers each has a width in a direction perpendicular to the wall surfaces that is less than a width of the building between opposite walls thereof. Thus, the interior perimeter barrier does not cover the entire surface of the soil in the interior of the building. If desired, however, a second interior barrier can be provided extending from the interior perimeter barrier adjacent each wall to the interior perimeter barrier adjacent the opposite wall. The second interior barrier can comprise a continuous film (for vapor barrier protection) or a mesh impregnated throughout with a synthetic pyrethroid insecticide. Furthermore, the interior and exterior perimeter barriers can comprise either a continuous film or a mesh. For example, it may be advantageous to use a mesh for the exterior perimeter barrier, as the mesh enables water to pass through the barrier such that landscape plants around the foundation can be properly irrigated.

Yet another aspect of the invention relates to the formation of thermal and insect barriers in spaces or cavities defined in a building structure. In accordance with the invention, such thermal and insect barriers are formed by injecting a foam-forming liquid composition into the space. The composition is operable to expand and to cure and harden to form a thermally insulating foam. The composition contains a synthetic pyrethroid insecticide mixed substantially homogeneously throughout the composition. The cured foam thus provides both thermal and insect barrier properties.

An apparatus for forming such barriers comprises a pressurized canister containing a liquid foam-forming composition operable upon release from the canister to expand and cure to form a hardened foam having thermal insulation properties, the foam-forming composition comprising a substantially homogeneous mixture of liquid foam-forming precursors and an insecticide from the pyrethroid family of insecticides. The apparatus further includes a dispenser coupled to the canister and operable to dispense the foam-forming composition therefrom. Advantageously, the canister has a relatively large capacity, such as about 20 gallons or more. However, for certain uses, such as injecting foam into an electrical junction box, it may be desirable to provide smaller hand-held canisters.

A still further aspect of the invention relates to agricultural applications where it is desirable to prevent insects from infesting certain areas near plants or in a yard. A significant problem affecting the nursery industry particularly in the southeastern part of the United States is the spread of imported fire ants. More specifically, seedlings are frequently raised and shipped in plastic pots. Fire ants can infest the soil in the pots, and it can be very difficult to eradicate them. Because shipment of pots infested with fire ants is a contributing factor in the continued spread of fire ants, it is illegal to ship nursery pots and plants out of a 13-state area of the southeastern U.S. without a certification from the USDA that the plants are "fire ant free". To combat this problem, the invention provides a container for plants comprising a polymer material shaped to define at least one receptacle for holding soil and a root system of a plant, the polymer material being impregnated throughout with an insecticide of the pyrethroid family. The insecticide is preferably permethrin and is present in a concentration of about 0.1-2.0 percent by weight, and more preferably about 0.3-1.0 percent by weight. Tests of the impregnated pots show they are very effective in preventing fire ant infestation.

The invention also includes methods for controlling insects on growing crops, as an alternative to fumigants such as methyl bromide or other compounds injected into the soil. In accordance with a preferred embodiment of the invention, a method for protecting a plant against crawling insects comprises disposing a sheet of polymer material proximate an upper surface of soil in which the plant is growing such that the sheet surrounds a base of the plant and extends outwardly therefrom. The polymer material is impregnated throughout with a synthetic pyrethroid insecticide. Preferably, the sheet consists essentially of a thermoplastic polymer composition formed into a sheet, a synthetic pyrethroid insecticide impregnated substantially uniformly throughout the sheet, from zero up to an effective amount of a colorant or pigment, and from zero up to an effective amount of a UV stabilizer for retarding degradation of the sheet from UV radiation. The sheet is disposed atop the upper surface of the soil. Larvae that fall from the plant are caught on the sheet, the insecticide being present in the sheet in an amount effective to kill the larvae that fall onto the sheet, whereby the sheet prevents the larvae from entering the soil, maturing to the adult stage, and laying eggs in the soil. The film also prevents adults from coming out of the soil. Where permethrin is the insecticide, an amount of insecticide effective to kill the larvae is about 0.1-2.0 percent by weight, more preferably about 0.3-1.0 percent by weight. Good results have been obtained with one percent concentration of the permethrin. The polymer sheet provides not only insect protection, but also provides the other beneficial functions of conventional plastic mulch. Moreover, preliminary tests indicate that virtually no, or only trace amounts, of residue of permethrin are detectable in soil that has been covered with the polymer sheet for an entire growing season. The essentially negligible residue, coupled with the well-established low toxicity of permethrin, make the method in accordance with the invention a safer alternative to insect control than injection of pesticides or other compounds into the soil.

A further aspect of the invention relates to providing protection for growing plants against ants, termites, and other crawling insects that may crawl up a trunk or stem of a plant and cause damage to the plant. For example, in the citrus industry, ants and termites can cause substantial damage to young citrus plants. Additionally, cold weather can also deleteriously affect the plants. The invention in a further embodiment provides a protective wrap and method for protecting a stem or trunk of a plant to discourage crawling insects from traveling up the trunk. The wrap can comprise a polymer film, mesh, or flexible foam material impregnated throughout with a synthetic pyrethroid insecticide. The wrap is wrapped about the circumference of the trunk or stem. The wrap preferably has a length of 4 to 24 inches, depending on the size of the plant to be protected. Where the wrap comprises a flexible foam material, the wrap preferably is configured in a hollow generally cylindrical shape with a longitudinal slit allowing portions of the wrap on either side of the slit to be spread apart for inserting the plant stem or trunk into the hollow interior of the wrap. Alternatively, the foam wrap can comprise a flexible sheet of foam material that is wrapped about the circumference of the trunk and secured in place in a suitable manner. The foam wrap provides both insect protection and thermal protection for the plant. The wraps can also protect against damage from impacts, such as from a lawn mower or gardening tool. The film and foam wraps further provide protection against the sun's rays, and also retard or prevent growth of new stems from the trunk.

A method for treating a grafted plant having a root stock portion and a grafted portion to retard or prevent growth of new stems from the root stock portion and to protect the plant from insects comprises wrapping the root stock portion above soil line with a wrap consisting essentially of a thermoplastic polymer composition, from about 0.1 to about 2.0 percent by weight permethrin impregnated substantially uniformly throughout the wrap, from zero up to an effective amount of a colorant or pigment, and from zero up to an effective amount of a UV stabilizer for retarding degradation of the wrap from UV radiation.

Yet another embodiment of the invention is useful for preventing and/or eliminating fire ant infestation of an area of ground. Fire ants colonies build mounds for housing the queen ant and the colony. The mounds usually protrude above ground level and are therefore readily detected. The invention provides a device for treating an ant hill to discourage ants from continuing to reside in the ant hill, comprising a stake adapted to be inserted into the ant hill, the stake being formed of a polymer material impregnated throughout with a synthetic pyrethroid insecticide. In a further embodiment, the stake further includes a cover attached to the stake and configured to cover at least a portion of the outer surface of the ant hill when the stake is inserted thereinto, the cover being formed of a polymer material impregnated throughout with a synthetic pyrethroid insecticide. Preferably, the stake is retrievable (i.e., it does not disintegrate in the soil) so that it can be removed when desired and then re-used, stored, or disposed of in a proper manner. The device is effective in causing the ant colony to abandon the hill, and thus can be useful in preventing or eliminating fire ant infestation from certain selected areas such as a garden, flower bed, children's play area, or the like.

BRIEF DESCRIPTION OF THE DRAWINGS

The above and other objects, features, and advantages of the invention will become more apparent from the following description of certain preferred embodiments thereof, when taken in conjunction with the accompanying drawings in which:

FIG. 15 is a perspective view of a plant container in accordance with the present invention;

FIG. 16 is a perspective view of a container for containing a plurality of plants in accordance with the invention;

FIG. 17 is a perspective view showing an agricultural mulching film in accordance with the invention installed at the base of a plant;

FIG. 18 is a cross-sectional view through an ant hill showing a stake in accordance with the invention inserted into the ant hill;

DETAILED DESCRIPTION OF THE DRAWINGS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
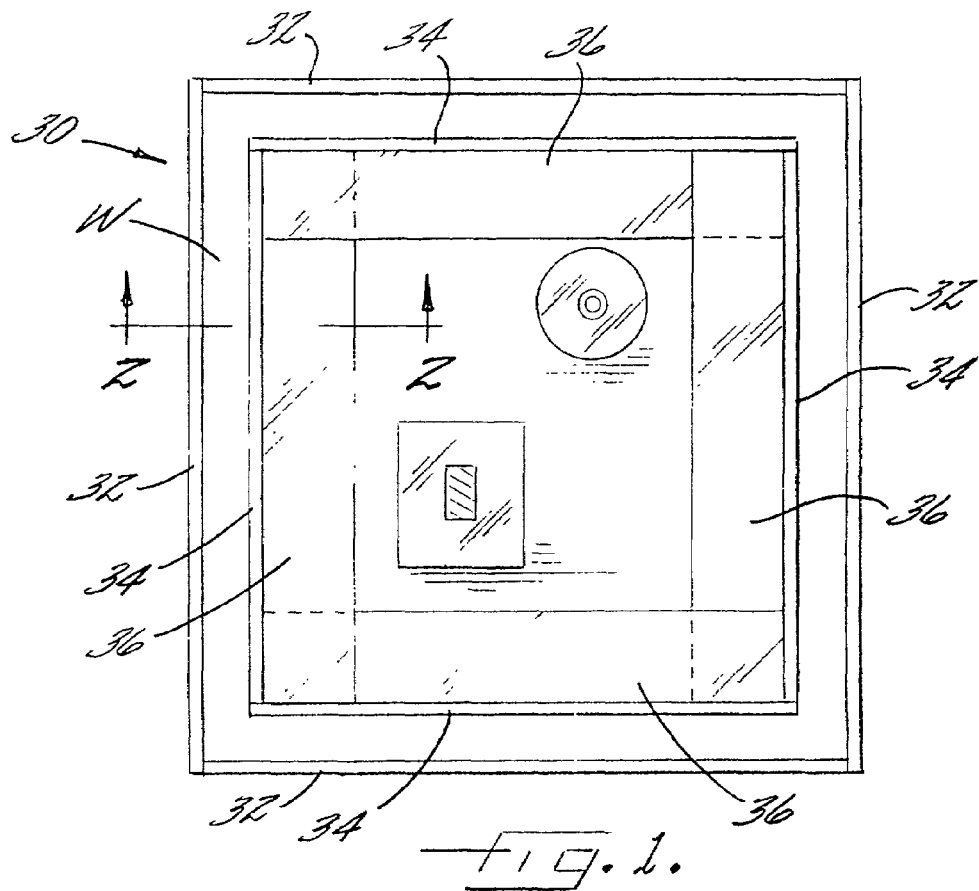
FIG. 1 is a top elevation of a thermal and insect barrier in accordance with a preferred embodiment of the invention installed in a building.
Figure 2:
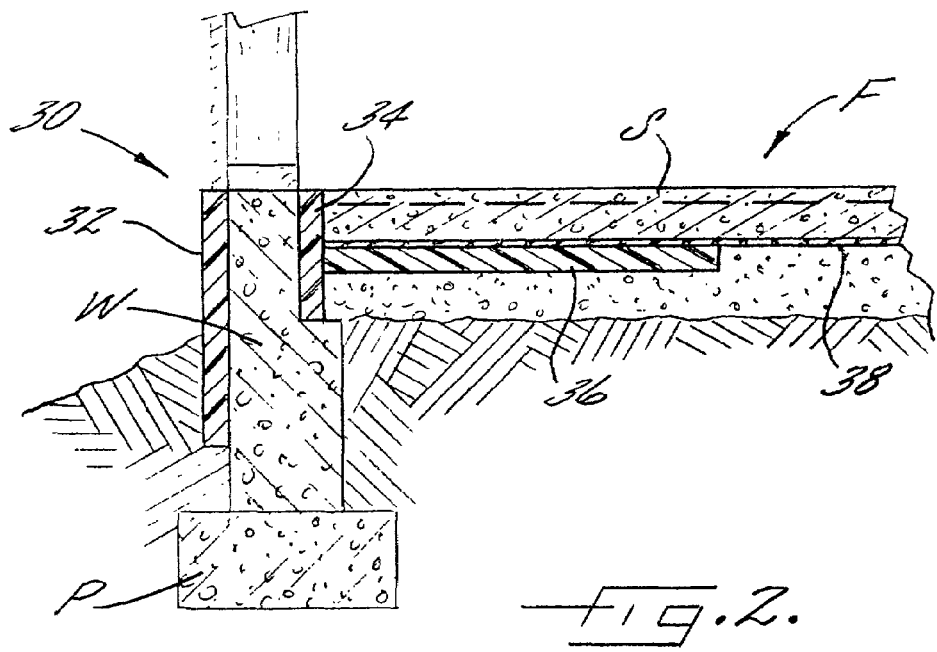
FIG. 2 is a cross-sectional view taken on line 2-2 of FIG. 1.

FIGS. 1 and 2 depict a preferred embodiment of the invention in the form of a thermal and insect barrier 30 for providing thermal and insect protection of a building structure built upon a slab-type foundation F. The foundation F typically includes vertical foundation walls W that extend around the perimeter of the foundation and are supported on footers or pads P. The foundation walls W usually have upper portions that extend above the grade level of the soil, and the building structure typically comprising wood-framed walls is built upon the upper portions of the foundation walls W and upon a horizontal floor or slab S that is poured upon a layer of suitable material such as gravel, sand, or the like. The outer perimeter of the slab S typically is supported upon or is adjacent the foundation walls W. In structures of this type, it is relatively easy for insects present in the soil to enter the building structure by burrowing and/or traveling along the surfaces of the foundation until they find an opening, such as an expansion crack or the like, through which they can pass into the building. Such openings are usually present particularly at the perimeter of the foundation where the slab meets the walls. Furthermore, at the exterior of the walls, there are abundant pathways along the exterior surfaces of the walls up to the building structure. The present invention seeks to protect the building structure from crawling insects by providing insect-repellant devices in particular locations where insects are particularly likely to enter the building. Thus, the thermal and insect barrier 30 includes a vertical thermal and insect barrier comprising exterior and interior foam sheets 32 and 34 respectively disposed on the exterior and interior surfaces of the foundation walls W. The foam sheets 32, 34 are formed of a rigid thermoplastic polymer foam such as polystyrene or an equivalent material providing thermal insulation properties. The foam material is impregnated throughout with an insecticide from the pyrethroid family of insecticides. Permethrin is a preferred insecticide, but other pyrethroids such as deltamethrin, bifenthrin, and others known to those of ordinary skill in the art can be used. Where permethrin is used, it preferably is present in a concentration of about 0.1 to 2.0 percent by weight of the foam material. The foam material optionally can also include a colorant or pigment for imparting any desired color to the foam, and a UV stabilizer for retarding degradation of the foam from UV radiation.

The foam sheets 32, 34 are located such that they extend above the grade level of the soil. Advantageously, the sheets should extend at least about six inches above grade, and more preferably at least about 12 inches above grade. The foam sheets 32, 34 cover substantially the entire exterior and interior perimeters of the foundation walls W. The interior foam sheets 34 may, if desired, be located between the interior surfaces of the walls W and the outer perimeter of the slab S as shown in FIG. 2. Alternatively, the interior foam sheets can extend upward to a point closely adjacent the lower surface of the slab. The foam sheets 32, 34 are located such that any insect pathway from soil along the walls W to the building structure must pass along the foam sheets. It has been found that many insects, including termites and fire ants, are repelled by the foam sheets and avoid coming into close proximity to the sheets. Accordingly, the foam sheets 32, 34 tend to prevent insects from entering the building along the foundation walls W. The foam sheets 32, 34 also provide thermal insulation of the foundation, which is an added benefit in terms of energy efficiency of the building structure. However, unlike conventional foam board or foam board impregnated with boric acid, the foam sheets 32, 34 do not provide a save haven for insects such as termites. On the contrary, termites and many other insects avoid coming close to the foam sheets and thus are deterred from trying to bore through the foam sheets or to build tunnels between the sheets and the foundation.

As an added measure of protection, the barrier 30 also includes a horizontal thermal and insect barrier comprising horizontal foam sheets 36 constructed similarly to the foam sheets 32, 34 and disposed adjacent a lower surface of the slab S between the soil and the slab. The horizontal sheets 36 extend about substantially the entire interior perimeter of the foundation adjacent the interior vertical foam sheets 34. Preferably, the outer edges of the sheets 36 abut the interior vertical sheets 34. The horizontal sheets 36 advantageously have a width at least about 36 inches, and more preferably about 48 inches. It is contemplated that foam sheets 36 in standard sizes of about 4 feet by 8 feet (or cut to size as needed) can be placed lengthwise along the interior perimeter of the foundation walls in end-to-end fashion on top of and level with the sand or gravel fill prior to the slab being poured, and the slab can then be poured in accordance with the usual practice.

If desired, an additional flexible insect barrier 38 can be disposed immediately adjacent the lower surface of the slab S. The flexible barrier 38 can comprise a continuous film of polymer material impregnated throughout with a synthetic pyrethroid insecticide. Alternatively, the flexible barrier 38 can comprise an open mesh formed of the polymer material impregnated with the insecticide. For instance, the mesh can have openings measuring about ⅛-inch to ¼-inch across. Where the flexible barrier is a continuous film, the film preferably has a thickness of about 0.004 to 0.010 inch, and more preferably about 0.006 to 0.008 inch. The mesh preferably has a thickness of about 0.0010 to 0.012 inch. The flexible barrier 38 can be formed of various thermoplastic polymers, including polyethylene, polypropylene, and others known in the art. The film or mesh preferably comprises about 0.1 to 2.0 percent by weight insecticide, and can optionally also include a colorant or pigment, and/or a UV stabilizer.

The foam sheets 32-36 and flexible barrier 38 are formed by incorporating the insecticide into the polymer composition such that the insecticide is substantially homogeneously mixed throughout the composition prior to the composition being shaped by extrusion or other suitable process into the final form of foam sheets, films, or meshes. Accordingly, the foam, film, and mesh are impregnated throughout with the insecticide.

Figure 3:
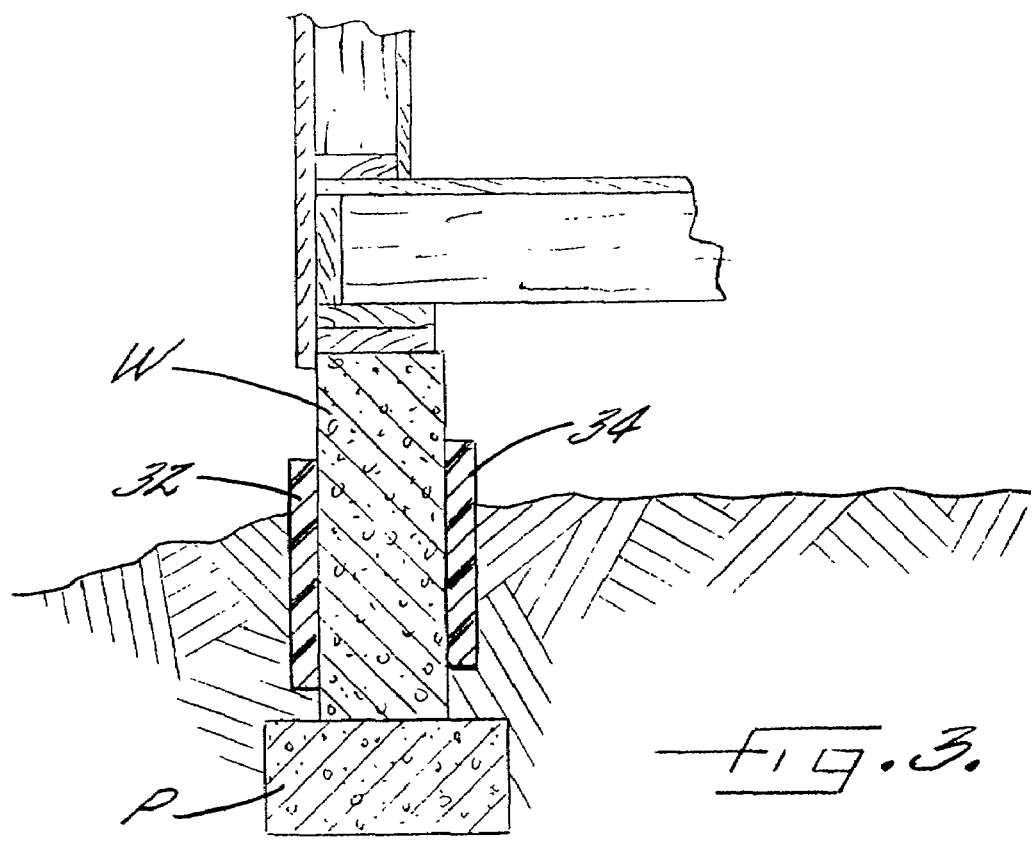
FIG. 3 is a cross-sectional view similar to FIG. 2, showing an alternative embodiment of the invention.

FIG. 3 depicts an alternative embodiment of the invention suitable for use with a building constructed upon a crawl space. Foam sheets 32 and 34 are installed against the exterior and interior surfaces of the foundation walls W as in the barrier of FIGS. 1-2. The foam sheets 32, 34 can be disposed partially below ground and extend above grade on both the exterior and interior surfaces of the walls. Preferably, the sheets 32, 34 extend above grade at least about 6 inches, and more preferably at least about 12 inches.

Figure 4:
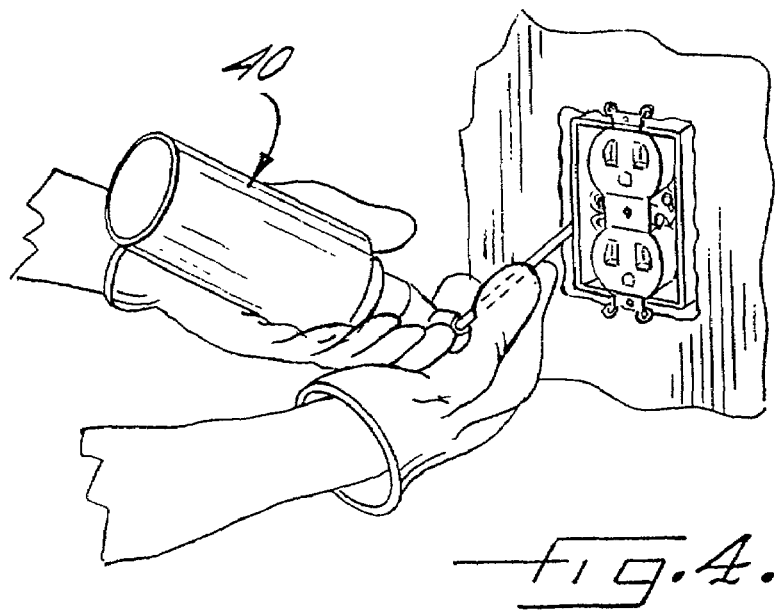
FIG. 4 is a perspective view showing application of a liquid foam-forming composition into a space within an electrical outlet.

Insulating foam can also be used in the form of an injectable liquid foam-forming composition having a synthetic pyrethroid insecticide homogeneously mixed throughout the composition. In accordance with a further aspect of the invention, such a liquid foam-forming composition is contained in a pressurized canister such that the composition can be dispensed and injected into a space or cavity within a building structure. FIG. 4 shows one potential usage of such a foam composition. A hand-held canister 40 containing a foam-forming liquid composition under pressure is used to inject a quantity of the composition into a cavity defined within an electrical outlet box such that the cavity is filled, upon the composition expanding and curing, with a foam impregnated throughout with insecticide. Suitable foam-forming compositions include polyurethane foam compositions that cure upon exposure to air and contain foaming agents such as dissolved hydrocarbons that volatilize and form bubbles upon release from the pressurized canister so as to cause foaming of the composition. A number of foam-forming compositions suitable for use with the invention are known to those of ordinary skill in the art, and thus are not further described herein. Liquid foam containing synthetic pyrethroid insecticide can also be injected into other types of electrical enclosures or boxes in accordance with the invention. For instance, in many outdoor electrical installations such as cable boxes, junction boxes for telephone lines, and the like, infestation of the boxes by insects can be a significant problem. Wasps, ants, termites, and many other types of insects often infest such boxes because they offer a protected space. Formosan termites are known to eat through insulation on electrical lines, and thus can pose substantial problems if they infest an electrical box. In accordance with the invention, liquid foam containing synthetic pyrethroid insecticide can be injected into an electrical box to serve as a long-term repellant tending to prevent infestation of the box by insects. Alternatively, a piece of rigid foam impregnated with synthetic pyrethroid insecticide or a piece of polymer film impregnated with synthetic pyrethroid insecticide can be placed inside the electrical box to serve the same purpose.

Figure 5:
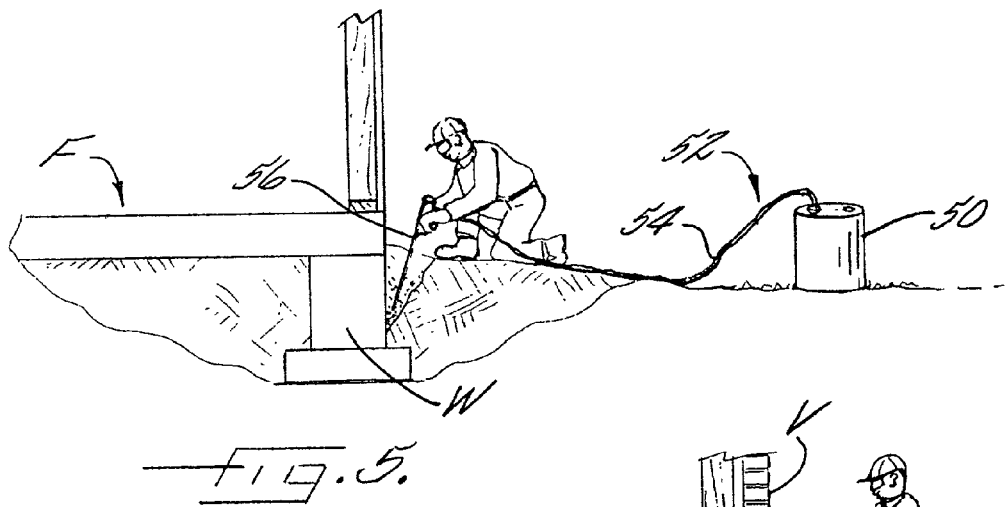
FIGS. 5-11 are schematic depictions of various applications of liquid foam-forming composition into cavities or spaces defined within various areas of building structures.
Figure 6:
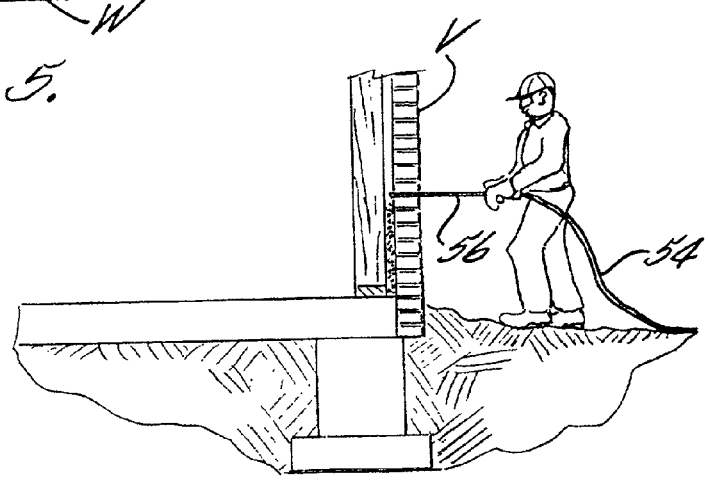
Figure 7:
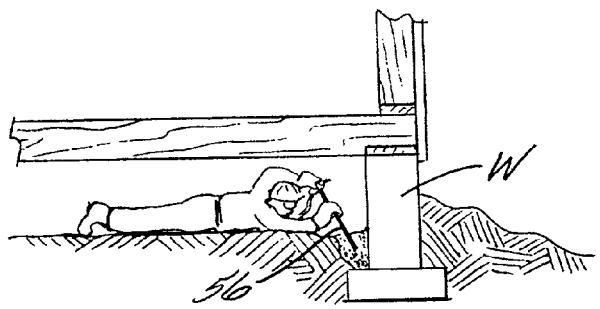
Figure 8:
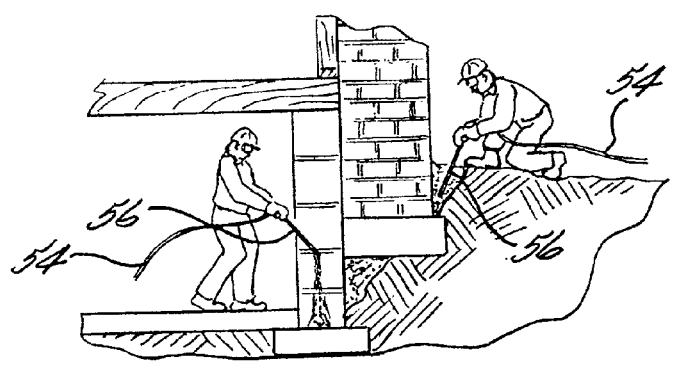
Figure 9:
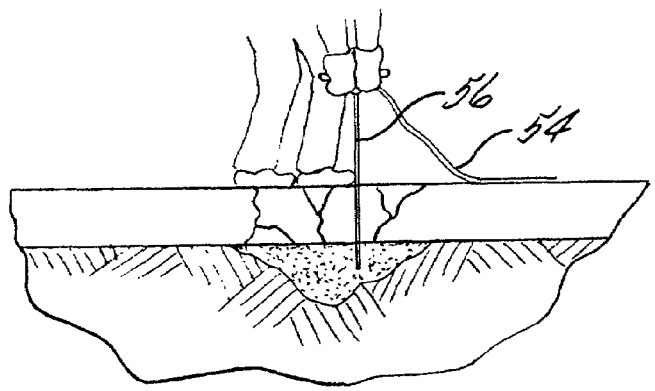

The invention also encompasses other apparatus and uses for the injectable foam-forming composition. FIGS. 5-11 depict a number of illustrative applications in which an insect-repellant insulating foam is formed within a space or cavity defined within a building structure. As shown in FIG. 5, for large-scale application of such a foam-forming composition, the composition is advantageously contained within a large-capacity pressurized canister 50, which preferably can contain 20 gallons or more of the liquid composition. The apparatus for injecting the composition also includes a dispenser 52, advantageously in the form of a flexible hose 54 and a dispensing nozzle 56 that can be inserted through an access hole drilled into the building such that the access hole opens into the space or cavity into which the foam-foaming composition is to be injected. For example, as shown in FIG. 6, an access hole can be drilled through an exterior brick veneer V so as to open into a space between the veneer V and the wall frame and the nozzle 56 can be inserted through the access hole such that an insect-repellant insulating foam can be injected into the space. FIGS. 5 and 7 show foam-forming composition being injected around the exterior and interior foundation walls, and FIG. 8 shows the spaces around a chimney being treated with foam-forming composition. FIG. 9 shows that an access hole can be drilled through a slab into a void beneath the slab, and the void can be filled with insect-repellant insulating foam. In some cases, a small air space may exist between the entire lower surface of a slab and the soil beneath the slab. This air space can be filled with foam in accordance with the invention, by drilling one hole through the slab into the space at a location near one edge of the slab, and drilling an air escape hole through the slab into the space near an opposite edge of the slab. Liquid foam-forming composition is then injected through the first hole. As the foam expands within the air space, air is allowed to escape from the air escape hole. When foam begins to come up through the air escape hole, the operator knows that the entire air space has been filled with the foam. The holes can then be plugged. The result is a permanent foam layer covering the entire under surface of the slab, providing long-term insect repellancy and thermal insulation.

Figure 10:
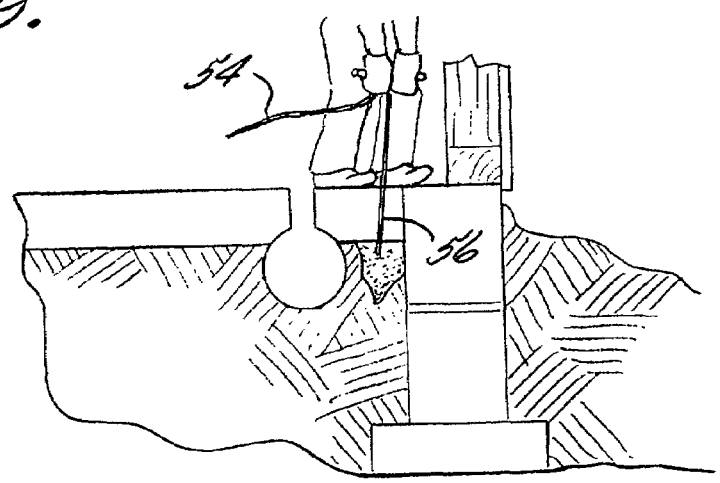
Figure 11:
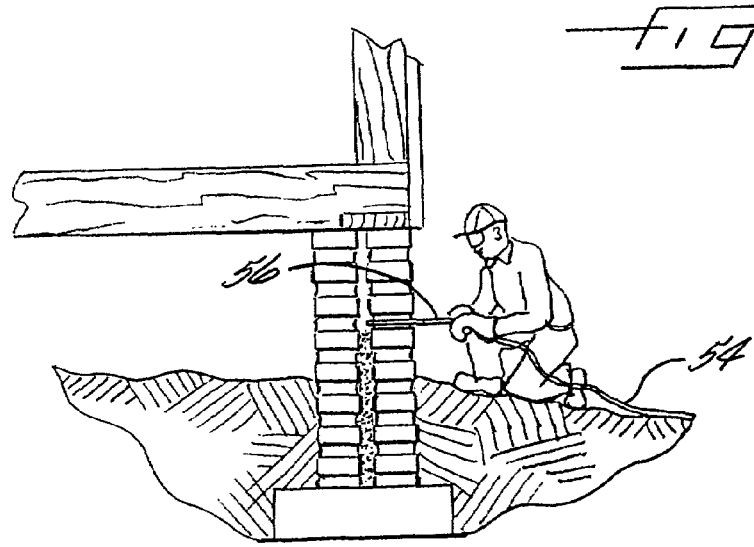

FIG. 10 illustrates a similar usage around a duct in a slab. FIG. 11 depicts a space within a brick pier being filled with an insect-repellant insulating foam in accordance with the invention.

Figure 12:
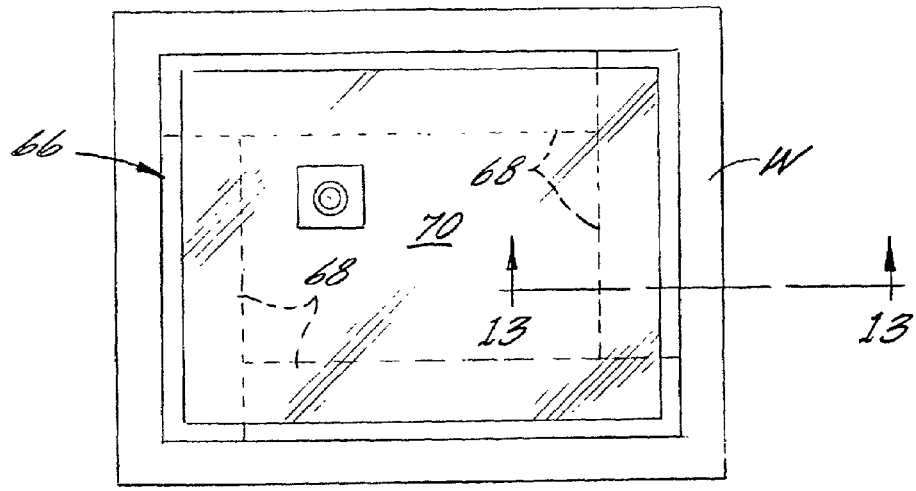
FIG. 12 is a top elevation of an insect barrier in accordance with yet another embodiment of the invention.
Figure 13:
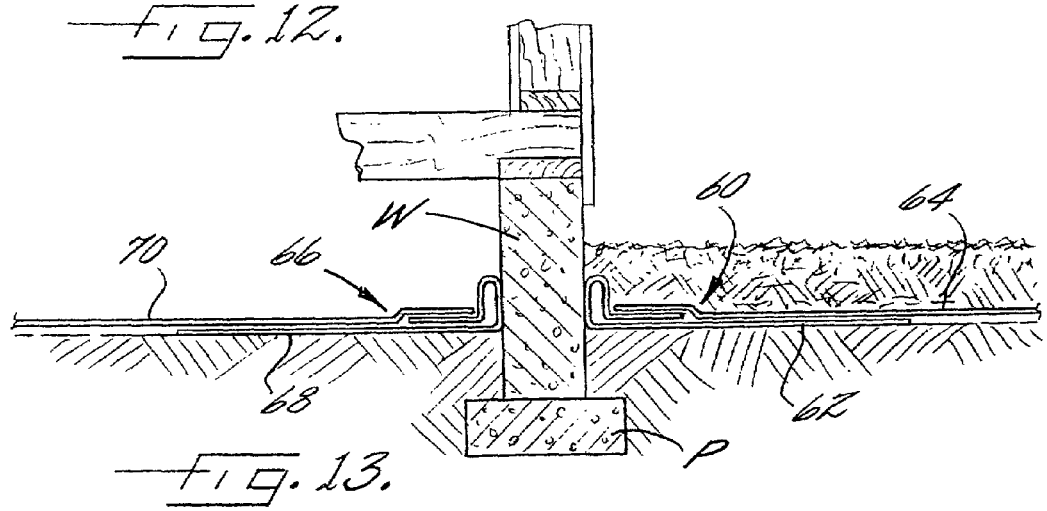
FIG. 13 is a cross-sectional view taken on line 14-14 of FIG. 13.

FIGS. 12 and 13 depict still another embodiment of the invention wherein polymer film sheets impregnated with a synthetic pyrethroid insecticide are used to construct external and internal perimeter barriers. An external perimeter barrier 60 is formed by disposing a sheet 62 along the entire external perimeter of a wall W proximate an upper surface of the soil. The sheet 62 has an inner portion that extends up the wall a predetermined height. The inner portion can be folded back on itself as shown in FIG. 13. The folded portion preferably extends outward from the wall for a distance of at least about 12 inches. Advantageously, a second sheet 64 is placed in overlapping relation to the first sheet 62 such that the inner portion of the second sheet 64 overlaps the folded portion of the first sheet 62. Alternatively, where the sheet material has sufficient width, a single sheet can be folded in a double-thickness to form a double-layered external perimeter barrier. The sheets 62, 64 can be covered with a thin layer (i.e., no deeper than about two inches) of soil or mulch. The external perimeter barrier 60 preferably extends outward from the wall W for a width of at least about 36 inches, and more preferably at least about 48 inches. The external perimeter barrier 60 preferably extends up the wall a height of at least about 6 inches.

A similar internal perimeter barrier 66 is formed by a first sheet 68 placed proximate the upper surface of the soil adjacent the interior perimeter of the walls W and extending up the walls W for a predetermined height, preferably at least about 6 inches. The first sheet 68 preferably has a width of at least about 36 inches, and more preferably at least about 48 inches. Advantageously, a second sheet 70 is placed overlapping the first sheet 68 in a manner similar to the external perimeter barrier, except that the second sheet 70 extends from the first sheet 68 adjacent one wall W to the first sheet 68 adjacent the opposite wall. As shown in FIG. 12, an additional sheet 72 can be used to surround a pipe 74 so as to form a skirt that extends outwardly from the pipe. Alternatively, a foam sheet can be used for this purpose as previously described.

Figure 14:
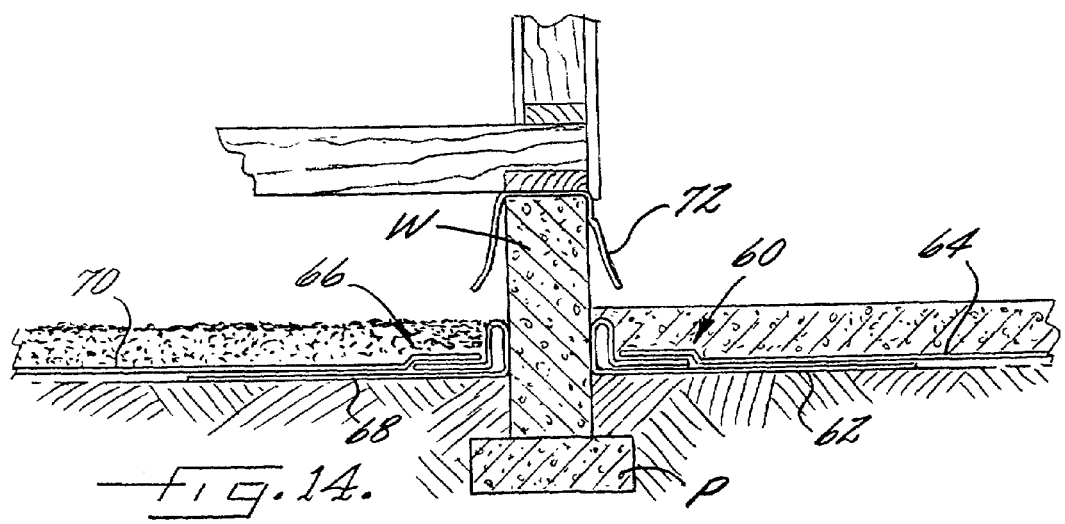
FIG. 14 is a view similar to FIG. 14, showing a still further embodiment of an insect barrier in accordance with the invention.

FIG. 14 shows yet another embodiment of an insect barrier for a building structure in accordance with the present invention. The barrier is similar to that shown in FIGS. 12 and 13, including external and internal perimeter barriers 60 and 66. The external barrier 60 is shown underlying a slab S forming a floor for a porch or the like. The internal barrier 66 is shown underlying a thin layer (up to about two inches in depth) of sand or the like within a crawl space of the building. Additionally, a hang skirt 76 is disposed atop a wall formed of blocks B such that the skirt 76 hangs down on both the exterior and interior sides of the blocks B and is located between the blocks B and the building structure built atop the wall of blocks. The hang skirt 76 is formed of a polymer film impregnated throughout with a synthetic pyrethroid insecticide.

Another aspect of the invention encompasses various devices for repelling insects in agricultural applications. As previously noted, fire ants represent a significant problem in the southeastern United States. The nursery industry is affected in that fire ants can infest nursery pots that are used for raising and transporting seedlings and other plants. All nursery pots and plants grown in a 13-state area of the southeastern U.S. cannot be legally shipped outside of this area unless they are certified "fire ant free" by the USDA. To help combat the problem of fire ant infestation, and with reference to FIG. 15, the present invention provides a plant container 80 (two different containers 80 shown) formed of a thermoplastic polymer composition impregnated substantially uniformly throughout with a synthetic pyrethroid insecticide, and optionally containing a colorant or pigment and a UV stabilizer. The insecticide preferably is present in an amount from about 0.1 to 2.0 percent by weight. The container 80 is of the type typically used for containing a single plant. The container 80 can be formed of any suitable polymer material including those materials commonly used for forming conventional plastic nursery pots, which are typically formed of thermoplastic polymers. FIG. 16 depicts a seedling tray 82 formed of the polymer material impregnated with the synthetic pyrethroid insecticide. The tray 82 has a plurality of receptacles for separately containing a plurality of individual seedlings.

Testing has been performed to determine the effectiveness of nursery pots impregnated with one percent permethrin by weight in preventing and/or eliminating infestation of imported fire ants. A number of both "treated" and "control" 1-gallon nursery pots were manufactured. The treated pots and control pots were both made of the same polyethylene composition, except that the treated pots were impregnated throughout with one percent by weight of permethrin by thoroughly mixing the permethrin with the polyethylene composition prior to formation of the pots. The treated and control pots were also colored differently to permit ready differentiation.

In a first series of tests conducted over a two-year period, imported fire ant colonies found in the field were dug up and the soil and ant colonies were placed in treated pots and control pots, one colony per pot. Each colony had at least 1000 ants. The colonies were selected from central Georgia (Atlanta and Macon areas) and from north central Florida (Gainesville and Keystone areas). A number of 20-gallon flat plastic tubs treated with powder to prevent the ants from escaping the tubs were used to contain the treated and control pots. In some of the tubs, two treated pots and two control pots were contained. In other tubs, one treated and one control pot were contained. The pots were spaced apart from each other in the tubs. Each "test" consisted of one tub containing the pots, and each test was conducted for 7 days, and then all colonies were observed for the number of active and live fire ants. Over the two-year period, a total of 32 treated pots and 32 control pots were tested in this manner. The test procedures used were consistent with those used by the USDA's Fire Ant Certification program. Of the 32 treated pots, none of the pots contained any active fire ants. Dead and inactive ants were found either outside the pots or within a central core of the soil in the pots. In contrast, of the 32 control pots, all colonies remained large and active and were aggressive when disturbed. Thus, the treated pots were quite effective in preventing the continued vitality of colonies contained in the pots.

In a second series of tests also conducted over a two-year period, 46 treated pots and 34 control pots were placed, upside down, over active fire ant hills that were located in the field so that each hill was covered by a pot. The pots did not penetrate the soil surface, but were merely placed atop the soil. The pots were left in place for 7 days, and then the ant hills were observed. Of the colonies covered by the 46 treated pots, all colonies had completely moved out from under the pots. It was noted that new colonies had formed nearby the original locations in each case, and it was presumed that the new colonies were the same colonies that had been under the treated pots. The abandoned hills under the treated pots were dry and devoid of all ants, and many dead ants were observed near the lips of the pots. In contrast, of the 34 control pots, all colonies remained large and active and were aggressive when disturbed, and the colonies had in fact expanded to fill the control pots.

FIG. 17 shows an agricultural mulching film 84 formed of polymer material impregnated with a synthetic pyrethroid insecticide for use in covering the soil beneath and around the base of a growing plant. The film 84 provides multiple benefits, including retention of moisture in the soil and inhibition of weed growth in the area covered by the film. Additionally, the film 84 repels insects. Furthermore, the film 84 can be effective in preventing the reproduction of crawling insects that feed on the above-ground parts of the plant. Typically, the larvae of such insects feed on the plant and then fall to the ground where they enter the soil and remain until they mature to the adult stage. The adults then lay more eggs in the soil around the plant. These eggs hatch to produce more larvae, which can then infest the plant and produce more damage. Multiple generations of insects can thus reproduce and continue to damage the plant. However, where the film 84 has been placed atop the soil around the plant, the larvae that fall from the plant are caught on the film 84. Because larvae are typically not very mobile, they tend to remain on the film. It has been found that a polyethylene film of 6 mils thickness and impregnated with one percent permethrin by weight can be effective in killing the larvae of many insects that fall onto the film, including cockroaches, termites, ants, sowbugs, caterpillars and beetle grubs. As a result, the larvae are not able to enter the soil and hence the film can prevent the reproduction of insects. Additionally, any adults that do mature in the soil under the film are repelled from exiting the soil into proximity with the film.

The film 84 preferably is formed of a composition including a thermoplastic polymer (e.g., polyethylene, polypropylene, or the like), a synthetic pyrethroid insecticide (preferably permethrin), optionally a colorant or pigment, and optionally a UV stabilizer for retarding degradation of the film from UV radiation. The coloring of the film can be selected to either absorb or reflect the sun's rays depending on the user's desires. For instance, a dark-colored film will tend to absorb the sun's rays and warm the underlying soil, while a light-colored film will tend to reflect the sun's rays and keep the soil cooler. A UV stabilizer can be included in the film if desired. However, it has been found that omitting the UV stabilizer can have advantages in that the film tends to become embrittled over time as a result of solar radiation.

By the end of a growing season, the film tends to become so brittle as to essentially disintegrate; the film can then be tilled into the soil rather than having to be removed and disposed of. Surprisingly, the soil itself nevertheless has virtually no residue of permethrin.

The film preferably contains about 0.1 to 2.0 percent by weight of the insecticide, and more preferably about 0.3 to 1.0 percent. The film preferably is provided in the form of a roll of continuous film material about 18 to 36 inches wide (more preferably about 20 to 24 inches wide) and as long as possible while maintaining a practically manageable diameter and weight of the roll. The roll can be used in existing film-laying machines that are used with conventional plastic mulch films. The film preferably has a thickness of from about 0.5 to 10 mils, more preferably about 0.5 to 3 mils.

The film impregnated with synthetic pyrethroid insecticide can also be useful in controlling fire ants. A series of tests were conducted to determine the effectiveness of an 8 mil-thick film of polyethylene impregnated with one percent by weight permethrin in eliminating fire ants from soil maintained adjacent the film. Both treated and control films were manufactured from essentially the same polyethylene composition, except for the inclusion of the permethrin in the treated film. The treated and control films were also colored differently for ready differentiation. In a first test procedure, fire ant hills located in the field were each covered with pieces of the film and the film pieces were held in place with rocks. Seventeen ant hills were covered with treated film, and 17 ant hills were covered with control film. After 7 days, the ant hills were observed. Of the 17 hills covered with treated film, all ant hills were inactive and devoid of ants. In the majority of these cases, new ant hills were observed within 2 to 15 feet of the original locations, and it was presumed that these were the same colonies that had moved from under the treated films. In 2 of the ant hills covered with treated film, there were no new ant hills observed nearby. Many dead fire ants were found on top of the treated films. In contrast, of the 17 ant hills covered with the control films, all ant hills remained large and active and the ants were aggressive when disturbed. It should also be noted that in some of the tests of the treated film, the tests were performed as much as 30 months after the film had been manufactured. Thus, the long-term efficacy of the film appears to be very good.

The present invention also provides a device for use in ant hills to eliminate infestation of the hills. As depicted in FIG. 18, the device comprises a stake 90 configured to be inserted into an ant hill such that the stake penetrates the hill to a substantial depth, for example to a depth of at least about six inches, and more preferably at least about twelve inches. The stake 90 is formed of a polymer material impregnated throughout with a synthetic pyrethroid insecticide, preferably permethrin. The permethrin is present in a concentration that is preferably less than two percent by weight, and more preferably about one percent by weight. The stake 90 can be formed of any suitable polymer, including polyethylene, polystyrene, or the like. The device can also include a cover 92 attached to the stake 90 and configured to cover at least a portion of the outer surface of the ant hill when the stake is inserted into the hill. The cover 92 is formed of a polymer film impregnated throughout with a synthetic pyrethroid insecticide, preferably permethrin in a concentration that is preferably less than two percent by weight, and more preferably about one percent by weight. The film cover 92 can be formed of any suitable polymer, including polyethylene, polypropylene, or the like.

Figure 19A:
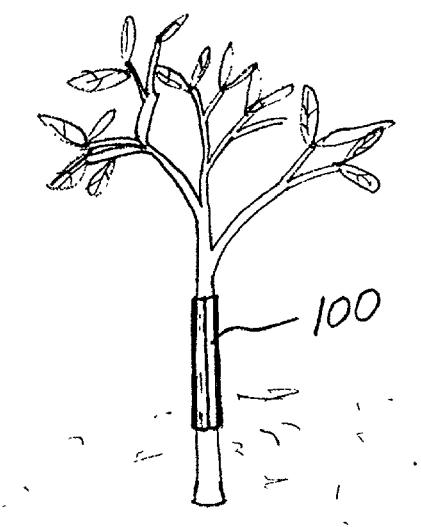
FIG. 19A shows a plant wrapped with a film wrap in accordance with a further embodiment of the invention.

The invention also encompasses protective wraps for wrapping about a trunk or stem of a growing plant to discourage crawling insects from traveling up the trunk and doing damage to the plant. FIG. 19A depicts a growing plant having a protective wrap 100 of polymer film impregnated throughout with a synthetic pyrethroid insecticide. The film can be formed in the manner previously described for the other films of the invention. The film wrap 100 comprises a generally rectangular piece of polymer film impregnated with the insecticide, the film being wrapped about the trunk of the plant to form a tube that encircles the circumference of the trunk. The film is secured in place in a suitable manner. For example, an adhesive material can be provided along one edge of the film so that this edge can be adhered to another portion of the film after the film is wrapped about the trunk. Alternatively, a wire or cord can be tied about the wrap to secure it in place. The wrap 100 preferably extends along a length of the trunk for at least about 4 inches; depending on the size of the plant, it may be desirable in some cases to have the wrap extend over a length of up to about 24 inches. The film advantageously has a thickness of about 6 to 12 mils. A protective wrap can also be formed from an open mesh of polymer material impregnated throughout with a synthetic pyrethroid insecticide. The mesh wrap is otherwise similar to the film wrap 100 in terms of construction and use.

Figure 19B:
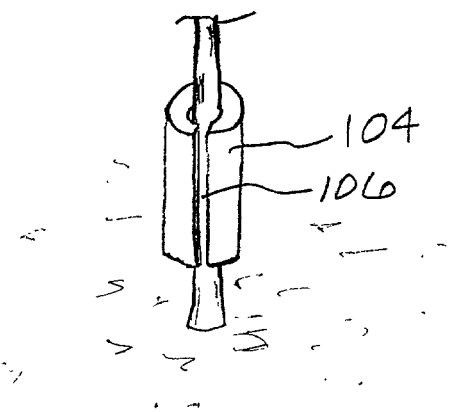
FIG. 19B shows a plant wrapped with a foam wrap in accordance with another embodiment of the invention.

FIG. 19B shows another embodiment of a protective wrap in the form of a flexible foam wrap 104. The foam wrap is formed of a flexible foam material impregnated throughout with a synthetic pyrethroid insecticide. For example, a flexible polyurethane foam material can be used for forming the foam wrap 104. The foam wrap 104, particularly for plants having trunks of small diameter, preferably is configured as a hollow cylinder having a longitudinal slit 106 along one side permitting the portions of the wrap on opposite sides of the slit to be spread apart so that the wrap can be fitted over the trunk. The foam material preferably is resilient so that after the trunk is inserted into the interior of the wrap 104, the wrap springs back toward its original shape and thus tends to snugly engage the trunk so that there are no large gaps between the trunk and the wrap. For larger diameter trunks, the foam wrap can be formed by a flexible sheet of foam material that is wrapped about the trunk and secured, similar to the film and mesh wraps described above. The foam wrap advantageously has a thickness of about ¼-inch to about 2 inches, depending on the overall length and width dimensions of the foam wrap. The foam wrap provides both insect protection and thermal protection for the plant. The film, mesh, and foam wraps can also protect against damage from impacts, such as from a lawn mower or gardening tool. The film and foam wraps further provide protection against the sun's rays, and also retard growth of new stems from the trunk. Thus, the wraps of the invention provide multiple benefits including insect repellancy.

The film or foam wrap also has application to grafted plants comprising a root stock portion and a grafted portion that is grafted into the root stock portion, as practiced for example in the citrus industry among others. In accordance with the invention, a method for treating a grafted plant to retard or prevent growth of new stems from the root stock portion and to protect the plant from insects comprises wrapping the root stock portion above the soil line with a wrap consisting essentially of a thermoplastic polymer composition, from about 0.1 to about 2.0 percent by weight permethrin impregnated substantially uniformly throughout the wrap, from zero up to an effective amount of a colorant or pigment, and from zero up to an effective amount of a UV stabilizer for retarding degradation of the wrap from UV radiation. The permethrin impregnated throughout the wrap repels insects so that the insects do not take up nesting between the wrap and the root stock portion. The wrap also prevents insects from crawling from the ground up the stem or trunk of the plant to the upper limbs.

It should also be apparent that the film, mesh, or foam wraps of the invention can be used in conjunction with the mulching film described above in connection with FIG. 18 to provide still further protection to a growing plant. The mulching film can comprise either a continuous film or an open mesh.

The invention also encompasses methods for packaging fresh produce (fruits and vegetables) to prevent insect infestation of the produce. In one method, produce items are placed within a shipping crate or box, which can be of wood, plastic, or other suitable materials. Typically the produce will first be placed in cartons of cardboard and the cartons will then be packed in the shipping crate. The crate will generally have six sides or faces, i.e., a horizontal bottom wall, four vertical side walls, and a horizontal top wall, although the top wall may be omitted if desired. At least four of the walls or sides of the crate are covered by a sheet material consisting essentially of a thermoplastic polymer composition, 0.1 to 2.0 percent permethrin impregnated substantially uniformly throughout the sheet material, and from zero up to an effective amount of a colorant or pigment. Preferably, the sheet material covers at least the four vertical side walls of the crate. The sheet material may be in the form of a continuous imperforate film or a perforated film or mesh to allow air circulation through the sheet material. The walls of the crate, as well as the cartons containing the produce, prevent direct contact between the sheet material and the produce, although it is believed such contact would not result in any significant residue of permethrin being transferred to the produce. The sheet material repels insects to prevent them from infesting the produce after it is packed in the crate. Additionally, any insects that may be on the produce before the sheet material is placed about the shipping crate will tend to be eliminated. The invention thus eliminates the need to spray the produce with insecticides before shipping.

In another method in accordance with the invention, a produce item or group of produce items is placed within a bag or sleeve consisting essentially of a thermoplastic polymer composition, from about 0.1 to 2.0 percent permethrin impregnated substantially uniformly throughout the bag or sleeve, and from zero up to an effective amount of a colorant or pigment. The bag or sleeve is formed of a sheet material, which can be a continuous imperforate film or a perforated film or mesh. The sheet material can be relatively thin, for example, about 0.5 to 2 mils. The bag or sleeve repels insects to prevent them from infesting the produce, and any insects that may be on the produce when it is placed in the bag or sleeve tend to be eliminated. The colorant or pigment can optionally be included to impart a particular color to the bag or sleeve, such as to identify the bag or sleeve as being a treated material as opposed to an ordinary bag or sleeve not containing insecticide. The colorant or pigment can be included in a small enough amount to preserve transparency of the bag or sleeve if desired, or can be added in greater amount to render the bag or sleeve substantially opaque if desired.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for protecting a growing plant against crawling insects during a growing season, comprising:
    disposing, atop the soil in which the plant is growing in the growing season, a single plastic sheet surrounding a base of the plant and extending outwardly therefrom, the sheet being formed from and consisting essentially of a polyethylene composition free of UV stabilizers such that the sheet readily degrades upon exposure to UV radiation, the polyethylene composition including polyethylene, and about 0.1 to 2.0 percent by weight of permethrin, the sheet being imperforate and impregnated substantially uniformly throughout with the permethrin and having a thickness of about 0.5 to 10 mils the sheet repelling the crawling insects while leaving virtually no residue of permethrin detectable in the soil that has been covered with the sheet.

2. The method of claim 1, wherein the sheet contains from about 0.3 to 1.0 percent permethrin.

3. The method of claim 1, wherein the sheet has a thickness of about 0.5 to 3 mils.

4. The method of claim 1 further comprising tilling the sheet into the soil at the end of the growing season.

5. The method of claim 1, further comprising the steps of allowing the sheet to degrade from UV radiation exposure until the sheet is substantially embrittled, and, at the end of the growing season, tilling the sheet into the soil.

6. The method of claim 5 wherein from about 0.3 to 1.0 percent by weight of the permethrin is impregnated substantially uniformly throughout the sheet.

* * * * *